United States Patent [19]

Martin et al.

[11] Patent Number: 5,816,701
[45] Date of Patent: Oct. 6, 1998

[54] AUTOMATED TABLET DISSOLUTION APPARATUS

[75] Inventors: Arthur L. Martin, Holliston; Richard S. Earle, Uxbridge; Warren P. Kerr, Concord; James L. Martin, Holliston, all of Mass.; Ronnie McDowell, Vauxhall; C. Darryl Morgan, Morristown, both of N.J.

[73] Assignee: Source For Automation, Inc., Holliston, Mass.

[21] Appl. No.: 691,407

[22] Filed: Aug. 2, 1996

Related U.S. Application Data

[63] Continuation-in-part of Ser. No. 635,863, Apr. 22, 1996, abandoned.

[51] Int. Cl.$^6$ ................................. G01N 1/38; B01F 1/00
[52] U.S. Cl. ........................ 366/208; 366/140; 366/142; 366/213; 73/61.71; 73/866; 422/270; 422/277
[58] Field of Search ...................... 366/140, 144, 366/150.1, 177.1, 178.2, 148, 145, 197, 198, 204, 207, 208, 184, 191, 241, 261, 285, 292, 342, 349; 422/62, 64, 68.1, 100, 101, 99, 209, 224, 225, 255, 261, 263, 268, 269, 270, 271, 272, 273, 275, 276, 277; 73/53.01, 866, 61.71

[56] References Cited

U.S. PATENT DOCUMENTS

| | | | |
|---|---|---|---|
| 2,843,169 | 7/1958 | Stein | 366/140 |
| 3,467,500 | 9/1969 | Wilkinson et al. | 366/140 |
| 3,791,222 | 2/1974 | Goodhart et al. | 73/866 |
| 3,802,272 | 4/1974 | Bischoff et al. | 73/866 |
| 4,681,858 | 7/1987 | Chaudhari et al. | 422/270 |
| 4,792,434 | 12/1988 | Metzger et al. | 422/283 |

(List continued on next page.)

OTHER PUBLICATIONS

Article entitled, "A fully automated, benchtop dissolution testing workstation," by Richard Buechsenschuetz, published before the present patent application.

Sales literature for Zymark Corp.'s Multidose workstation, published before the present patent application.

Sales literature for Scientific Instruments and Technology Corp.'s PHARMA TEST dissolution baths, published before the present patent application.

*Primary Examiner*—Tony G. Soohoo
*Attorney, Agent, or Firm*—Kriegsman & Kriegsman

[57] ABSTRACT

In a preferred embodiment, the apparatus includes a dissolution vessel removably seated within an aluminum platen. The apparatus also includes an assembly for automatically measuring a desired volume of media, heating and degassing the volume of media and then dispensing the volume of media into the dissolution vessel. In addition, the apparatus includes a carousel having a plurality of compartments, the carousel being rotatably mounted on a stage, the stage being alignable with the vessel. According to one mode of operation, an open-top, cage-type basket is placed in one or more compartments of the carousel, each basket containing a tablet intended for dissolution. The apparatus additionally includes a shaft aligned with the vessel, the bottom end of the shaft being adapted to frictionally fit together with a basket. The shaft is rotatable and vertically movable so that it can fit together with a basket, pick the basket up out of the carousel, lower the basket into the vessel, rotate the basket within the media and remove the basket from the media. The apparatus further includes a catheter automatically movable in and out of the vessel for sampling the media at desired times, an automated mechanism for loading and replacing a depth filter on the input end of the catheter, an automated mechanism for removing the basket from the end of the shaft after testing has been completed and an automated mechanism for removing media from the vessel after testing has been completed. The apparatus also includes a paddle shaft which may be used interchangeably with the basket shaft if tablets are placed directly in the compartments of the carousel and are then dispensed from the carousel into the vessel through an opening in the bottom of each carousel that is alignable with an opening in the stage.

25 Claims, 10 Drawing Sheets

U.S. PATENT DOCUMENTS

| | | | |
|---|---|---|---|
| 4,856,909 | 8/1989 | Mehta et al. | 366/208 |
| 4,879,917 | 11/1989 | Eppelmann et al. | 73/866 |
| 4,924,716 | 5/1990 | Schneider | 73/866 |
| 5,076,107 | 12/1991 | Timmermans et al. | 73/866 |
| 5,174,508 | 12/1992 | Martin . | |
| 5,380,485 | 1/1995 | Takhashi et al. | 422/62 |
| 5,403,090 | 4/1995 | Hofer et al. | 366/207 |

AUTOMATED TABLET DISSOLUTION APPARATUS

CROSS-REFERENCE TO RELATED APPLICATIONS

This application is a continuation-in-part of U.S. patent application Ser. No. 08/635,863, filed Apr. 22, 1996, now abandoned which is incorporated herein by reference.

BACKGROUND OF THE INVENTION

The present invention relates generally to tablet dissolution testing and more particularly to a novel tablet dissolution apparatus.

In the pharmaceutical industry, it is commonplace, during pharmaceutical formulation development, stability determination, analytical development, quality control, or otherwise, to ascertain the rate at which a drug in solid form (hereinafter referred to as a "tablet") dissolves under certain well-defined conditions. In this manner, one can gauge or predict the dissolution rate of the tablet in the human stomach. Historically, tablet dissolution testing has been performed largely manually and has required a person to perform the following type of procedure: First, the person pours a defined volume (e.g., approximately 500–1000 ml) of an appropriate medium, such as water or a pH-adjusted buffer, into a 1 liter vessel positioned in a water bath, the water bath typically being heated to about 37° C. The person then drops a tablet to be tested into the media and lowers a mechanically-rotating paddle (rotating at approximately 50–150 rpm) into the media to stimulate dissolution of the tablet. (As an alternative to dropping the tablet into the media and using a paddle to stimulate dissolution, the person may place the tablet inside a cage-type basket, which is then lowered by the person into the media and mechanically rotated at about 50–150 rpm.) At one or more defined times (typically between about 0.5–2 hours after the tablet is dropped into the media), the person withdraws and filters one or more samples of the media from the vessel (typically using a depth filter fitted on the end of a suctioning sampling tube inserted into the media). The person then analyzes each filtered sample (e.g., using UV spectrophotometry, high performance liquid chromatography (HPLC), etc.) to detect the level of drug dissolved therein.

Frequently, it is necessary for the person to repeat the aforementioned dissolution procedure for a plurality of tablets, it therefore being further necessary, between successive tests, for the person to empty and to wash the vessel, to wash the paddle and to replace the media in the vessel.

To enable several tablets to be dissolved at the same time (i.e., in a batch mode), semi-automated dissolution equipment has been developed. Such equipment (e.g., VanKel, Edison, N.J ; DISTEK, New Brunswick, N.J.; Hanson, Chatsworth, Calif.) typically includes a plurality of vessels (e.g., six) positioned in a water bath and a corresponding plurality of rotatably-driven paddles or baskets positionable in the vessels. (Instead of employing a water bath to heat the media-filled vessels, the dissolution equipment may alternatively use one or more ceramic platens fixed to the outside of each vessel-DISTEK, New Brunswick, N.J.) Nevertheless, as can readily be appreciated, even the above-described equipment requires a great deal of manual labor, as the sampling step, as well as the vessel emptying, filling and washing steps, among other things, are still performed manually.

Consequently, dissolution testing has traditionally been labor-intensive, slow and prone to the commission of errors.

Recently, however, efforts have been undertaken to automate as many aspects of dissolution testing as possible. An example of such efforts is the MultiDose™ workstation of Zymark Corporation, Hopkinton, Mass. The MultiDose™ workstation, which is adapted for integration with commercially-available, multi-vessel, dissolution testing equipment of the type described above, includes a plurality of rotatably-driven carousels which are positioned over a corresponding plurality of vessels. Each carousel is adapted to hold a plurality of tablets. The workstation further includes automated means for dispensing a gravimetrically-measured quantity of media into each of the vessels, automated means for causing each of the carousels to drop a tablet into its corresponding vessel at a desired time, automated means for causing each of the paddles to rotate within its respective vessel, automated means for sampling the media from each of the vessels at one or more desired times, automated means for filtering the sampled media prior to analysis and automated means for emptying and washing the vessels between successive tests.

Although the above-described MultiDose™ workstation represents an advance in the art of dissolution testing technology, the present inventors have identified certain shortcomings in the MultiDose™ workstation. One such shortcoming is that the MultiDose™ workstation is designed for use in combination with pre-existing, commercially-available, six-vessel dissolution equipment of the type described above. The present inventors believe that this is a shortcoming for the following reasons: First, the combination of the MultiDose™ workstation and the above-described six-vessel dissolution equipment is rather expensive and occupies a considerable amount of laboratory space; consequently, certain small laboratories may be unable to use such equipment due to price and/or space considerations. In addition, even though there are instances where less than all six vessels need to be used at the same time for dissolution testing, certain components of the six-vessel dissolution equipment are not capable of being operated independently for each of the six vessels; consequently, some of the equipment must be used even when not needed. Moreover, because the MultiDose™ workstation performs the emptying, washing and filling steps for all six vessels at the same time, a second batch of tablets cannot be tested until all of the testing for the first batch of tablets has been completed. Furthermore, whereas approximately 50% of dissolution testing in the art is currently performed using the above-mentioned basket method (as opposed to the paddle method), the MultiDose™ workstation is adapted for use only with paddle-type systems. Other shortcomings will be described or will be apparent from the discussion below.

SUMMARY OF THE INVENTION

It is an object of the present invention to provide a novel tablet dissolution apparatus.

It is another object of the present invention to provide a tablet dissolution apparatus that overcomes at least some of the shortcomings inherent in existing tablet dissolution apparatuses.

It is still another object of the present invention to provide a tablet dissolution apparatus that is compact in size and easy to use.

According to one aspect of the invention, there is provided a tablet dissolution apparatus that is alternately configurable for either paddle-type or basket-type dissolution of a tablet.

According to another aspect of the invention, there is provided a tablet dissolution apparatus that includes automated means for volumetrically measuring and dispensing a quantity of dissolution media into a dissolution vessel.

According to yet another aspect of the invention, there is provided a tablet dissolution apparatus that includes automated means for preheating dissolution media to a temperature approximating that desired for dissolution and for dispensing such preheated dissolution media into a dissolution vessel.

According to still another aspect of the invention, there is provided a tablet dissolution apparatus that includes a dissolution vessel and a metal platen, the metal platen being used, instead of a water bath, to heat the contents of the dissolution vessel.

According to still yet another aspect of the invention, there is provided a tablet dissolution apparatus that includes a dissolution vessel and a platen for heating the contents of the dissolution vessel, the platen being sized and shaped to removably receive the dissolution vessel.

According to a further aspect of the invention, there is provided a tablet dissolution apparatus that includes fully-automated means for withdrawing and filtering a sample from a dissolution vessel, said fully-automated means including a depth filter positioned on the end of a sampling tube inserted into the dissolution vessel.

According to yet a further aspect of the invention, there is provided a tablet dissolution apparatus that enables the fully-automated, serial, basket-type dissolution of a plurality of tablets in the same dissolution vessel.

According to still yet a further aspect of the invention, there is provided a tablet dissolution apparatus that includes camera means for imaging the contents of a dissolution vessel for purposes of enabling verification of proper placement of the tablet and the paddle or basket within the vessel.

According to even yet a further aspect of the invention, there is provided a tablet dissolution apparatus that includes a media removal assembly comprising the combination of a comparatively large-diameter media removal tube and a comparatively-small diameter media removal tube.

According to still even yet a further aspect of the invention, there is provided a tablet dissolution apparatus that includes a first dissolution vessel, a second dissolution vessel and commonly-controlled automated means for causing the dissolution of a first tablet in said first dissolution vessel and for causing the dissolution of a second tablet in the second dissolution vessel wherein the respective dissolutions of the first and second tablets are operable completely independently of one another.

Additional objects, as well as features, advantages and aspects of the present invention, will be set forth in part in the description which follows, and in part will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate a preferred embodiment of the invention and, together with the description, serve to explain the principles of the invention. In the drawings wherein like reference numerals represent like parts.

DETAILED DESCRIPTION OF PREFERRED EMBODIMENTS

Referring now to FIGS. 1 through 5, there are shown various views of one embodiment of an automated tablet dissolution apparatus constructed according to the teachings of the present invention, the automated tablet dissolution apparatus being represented generally by reference numeral 11. Those aspects of apparatus 11 not pertinent to the present invention are neither shown in the drawings nor described herein for clarity.

Apparatus 11 includes a housing 13, which may be made of metal or a similarly suitable structurally-durable material. Housing 13 includes an upper portion 15 and a lower portion 17, upper portion 15 and lower portion 17 being separated by a platform 19. A drawer 21 is mounted within lower portion 17 of housing 13, drawer 21 being manually slidabllle forwards and backwards within lower portion 17 in the directions indicated by arrows A and A', respectively, for reasons hereinafter to become apparent.

Figure 6:
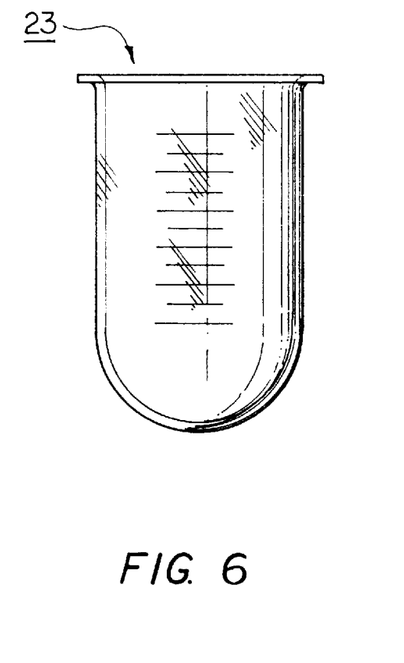
FIG. 6 is an enlarged front elevation view of the dissolution vessel of the automated tablet dissolution apparatus of FIG. 1.
Figure 7:
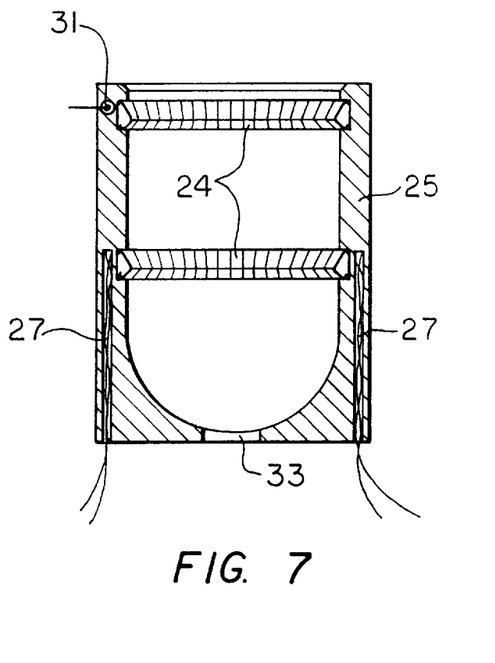
FIG. 7 is a partly schematic section view of the dissolution vessel heating assembly for the apparatus of FIG. 1.
Figure 8:
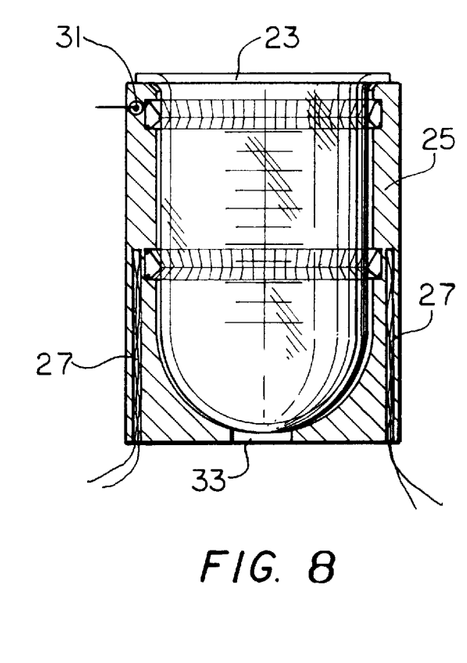
FIG. 8 is a view, partly in section, of the dissolution vessel of FIG. 6 removably seated within the platen of the heating assembly of FIG. 7.
Figure 9:
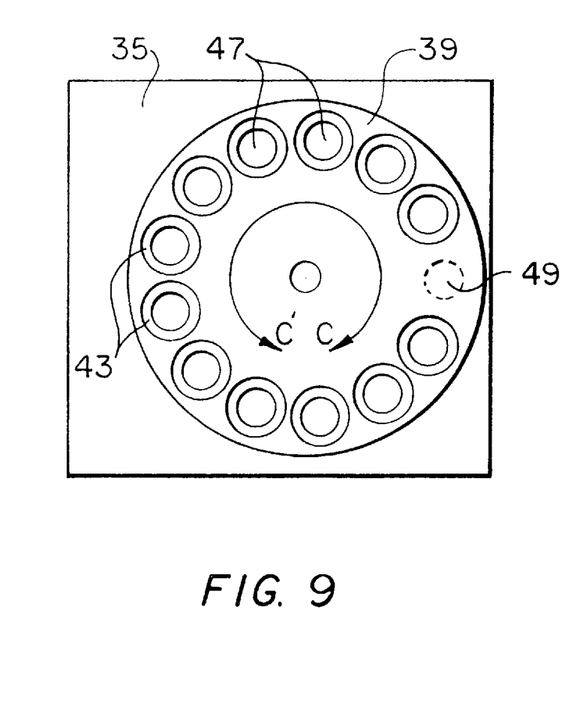
FIG. 9 is a plan view of the stage, carousel and carousel motor shown in FIG. 1.
Figure 10:
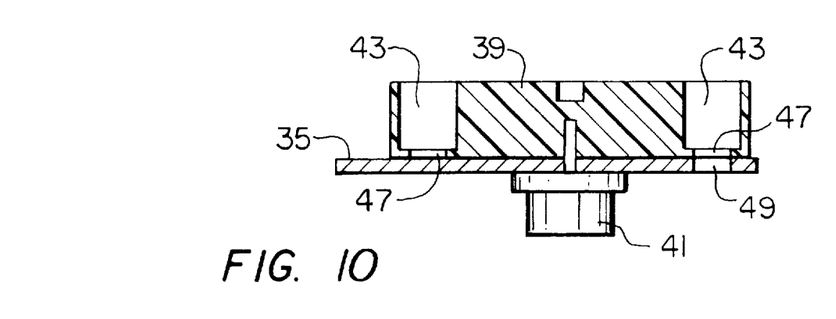
FIG. 10 is a section view of the assembly of FIG. 9, with one of the compartments of the carousel being shown aligned with the tablet opening in the stage.
Figure 11:
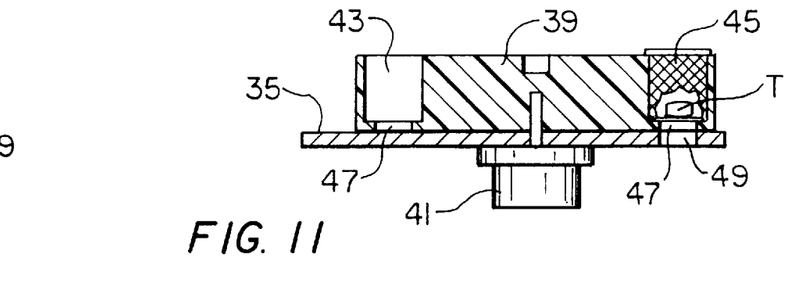
FIG. 11 is a section view, broken away in part, of the assembly of FIG. 9; a tablet-containing basket being shown loaded into one of the compartments of the carousel.

Apparatus 11 also includes a dissolution vessel 23 (seen best in FIG. 6). In the present embodiment, vessel 23 is a 1 liter transparent glass vessel of the type conventionally used in tablet dissolution apparatuses. Apparatus 11 additionally includes means for heating the contents of dissolution vessel 23. Referring now to FIGS. 7 and 8, in the present embodiment, said means for heating the contents of dissolution vessel 23 can be seen to include a metal platen 25. Platen 25, which is preferably made of aluminum or a similarly suitable heat-conductive material, is appropriately sized and shaped to removably receive vessel 23. A plurality of heat-conductive fingers 24 used to promote heat transfer from platen 25 to vessel 23 are affixed to the interior surface of platen 25 and are adapted for contact with vessel 23 when vessel 23 is seated within platen 25. A plurality of resistive heating elements 27 are disposed within platen 25 to heat platen 25. The outputs of elements 27 are controlled by a computer 29 (see FIG. 1). (For convenience and clarity, certain connections between computer 29 and other components of apparatus 11 are not shown.) A thermistor 31, which is also connected to computer 29, is also disposed within platen 25 to determine the temperature of platen 25. In this manner, using suitable calibration curves, computer 29 can be used to control the temperature at which the contents of vessel 23 are maintained by monitoring the temperature of platen 25 with thermistor 31 and accordingly adjusting the outputs of heating elements 27. Typically, the contents of vessel 23 are maintained at a temperature of 37° C.

Referring back now to FIGS. 1 through 3, vessel 23 and platen 25 can be seen to be positioned within the rear of drawer 21. Vessel 23 can be removed from apparatus 11 (e.g., for washing or replacement) by pulling drawer 21 forwardly in the direction of arrow A and lifting vessel 23 out of platen 25.

An opening 33 is provided in the bottom of platen 25. A camera 34, which is controlled by and whose output is fed to computer 29, is aligned with opening 33 so that one or more images, as desired, may be taken of the contents of vessel 23. Such images may be stored in computer 29 (and, if desired, printed out by a printer (not shown) connected to computer 29) and may be used, for example, to verify that a tablet was dropped correctly into vessel 23 and/or that the tablet was dissolved properly. Although not shown, one or more openings like opening 33 may be provided in the side wall of platen 25 to permit an additional camera to be deployed from a different vantage point than that of camera 34 or to permit an individual to visually inspect the contents of vessel 23.

Figure 12:
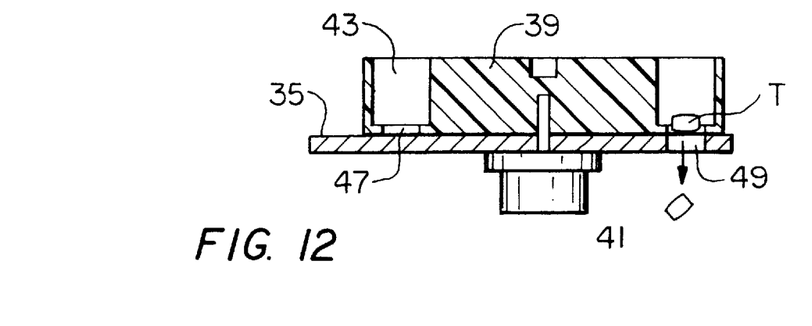
FIG. 12 is a section view of the assembly of FIG. 9, a tablet being shown loaded into one of the compartments of the carousel to illustrate how a tablet may be dispensed from the carousel through the tablet opening in the stage.

Apparatus 11 further comprises a stage 35 disposed within drawer 21. Stage 35 is mechanically coupled to an air cylinder 37. Air cylinder 37, which is controlled by computer 29, moves stage 35 forwards and backwards within drawer 21 in the directions indicated by arrows B and B', respectively. A carousel 39 is rotatably mounted on top of stage 35. Rotation of carousel 39 in the directions indicated by arrows C and C' is caused by a motor 41, which is controlled by computer 29. Referring now to FIGS. 9 through 12, additional details of stage 35 and carousel 39 are shown. As can be seen, carousel 39 is shaped to include a plurality of compartments 43. Each compartment 43 is appropriately dimensioned to removably receive a cagetype, open-top basket 45 (see FIG. 11) adapted to hold a tablet T (to enable apparatus 11 to be used for basket-type dissolution). In addition, the bottom of each compartment 43 is provided with an opening 47 sufficiently large to permit a tablet T to pass therethrough but small enough to prevent basket 45 from passing therethrough. An opening 49 appropriately dimensioned to permit tablet T to pass therethrough is also provided in stage 35. Opening 49, which is aligned with vessel 23 when stage 35 is in its rearwardmost position within drawer 21, may be aligned with opening 47 of each compartment 43 by rotating carousel 39. In this manner, as can be seen in FIG. 12, when a basket-less compartment 43 containing a tablet T is aligned with opening 49, tablet T can drop through openings 47 and 49 (and into vessel 23) to enable apparatus 11 to be used for paddle-type dissolution.

Referring back now to FIGS. 1 through 3, apparatus 11 further comprises means for dispensing a volumetrically-measured quantity of pre-heated, sparged (i.e., de-gassed) media into vessel 23. As can best be seen in FIGS. 13 and 14, said dispensing means comprises, in the present embodiment, a cylindrical platen 51, which is preferably made of aluminum coated with TEFLON (synthetic resin polymer) or a similarly suitable heat-conductive, non-stick surface. A plurality of resistive heating elements 53, connected to and controlled by computer 29, are disposed within platen 51. Platen 51 is mounted on top of a base member 57, and a cover 59 is mounted on top of platen 51. Platen 51, base member 57 and cover 59 jointly define a media chamber 61. Media is introduced into chamber 61 from an external source (not shown) through tubing 63 inserted into a media input channel 65 formed in base member 57. Once in chamber 61, the media is pre-heated via platen 51 to a temperature slightly higher than that desired for dissolution (e.g., about 38° C.) so that, during transport from chamber 61 to vessel 23, the media may cool to the appropriate dissolution temperature. Helium, which is added to the media in order to sparge (i.e., de-gas) the media, is introduced into chamber 61 from an external source (not shown) through tubing 67 inserted into a helium input channel 69 formed in base member 57.

Figure 13:
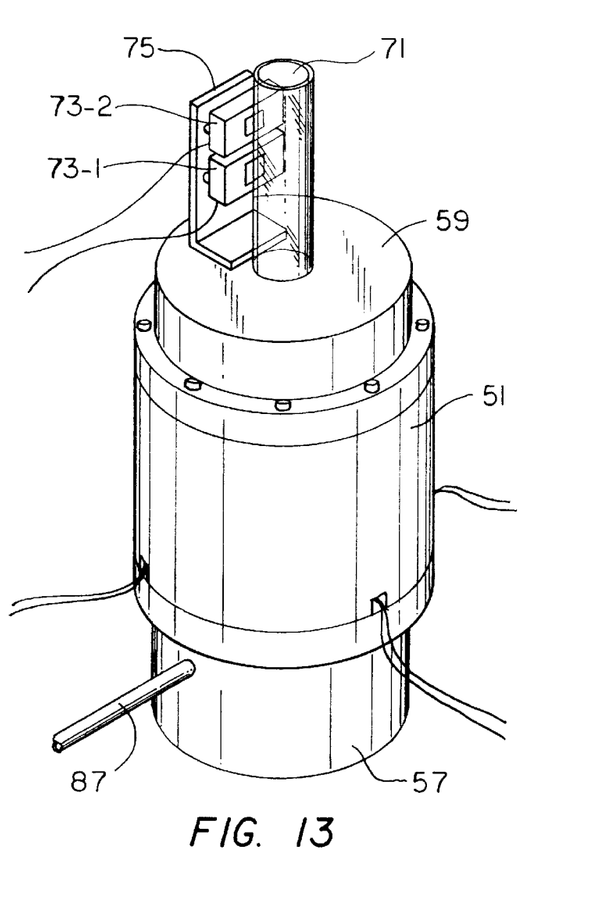
FIG. 13 is an enlarged perspective view of the assembly shown in FIG. 1 for preheating, sparging and dispensing a volumetrically determined quantity of media into the dissolution vessel.
Figure 14:
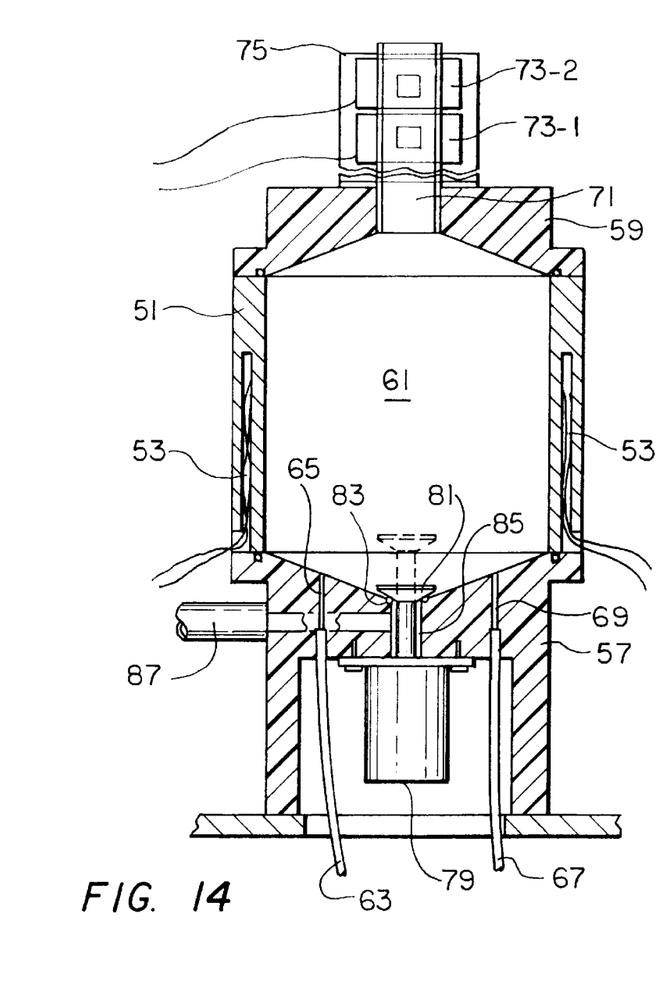
FIG. 14 is a section view of the preheating, sparging and dispensing assembly shown in FIG. 13.

A section of clear tubing 71 is mounted within cover 59 so that one end thereof is placed in fluid communication with chamber 61 and so that the other end thereof extends upwardly a short distance beyond the top of cover 59. A pair of media detectors 73-1 and 73-2, which are connected to computer 29, are mounted on a bracket 75 extending parallel to tubing 71. Detector 73-1 is appropriately vertically positioned on bracket 75 so that, when detector 73-1 detects media at a corresponding height in tubing 71, a signal is sent to computer 29 indicating that a desired volume of media (e.g., about 900 ml) is present within chamber 61 and tubing 71. Computer 29 then shuts down the flow of additional media into chamber 61 through tubing 63 (by means of a valve not shown). Detector 73-2, which is vertically positioned higher on bracket 75 than is detector 73-1, detects when the aforementioned volume of media has expanded due to having been pre-heated to a desired temperature, e.g., about 38° C. When detector 73-2 detects media at the appropriate level, it sends a signal to computer 29. Computer 29 then causes a motor 79 to drive a piston 81 upwardly and away from an O-ring 83 located at the entrance of a media egress channel 85 formed in base member 57. With piston 81 spaced apart from O-ring 83, media is then allowed to escape from chamber 61 and is conducted through channel 85 into vessel 23 via a media dispensing tube 87.

As can readily be appreciated, the above-described media dispensing means can be modified to measure varying volumes of media by providing a movable piston within chamber 61 that effectively varies the usable volume of chamber 61.

Referring back now to FIGS. 1 through 5, apparatus 11 further comprises a basket shaft 91. Basket shaft is vertically aligned with vessel 23 and with opening 49 of stage 35 (when stage 35 is in its rearwardmost position) and has a bottom end in the form of a basket lid 93. Lid 93 is appropriately dimensioned to engage a basket 45 from the top by friction-fit. Near its top end 95, basket shaft 91 is removably attached by walking collars (not shown) to a carriage 97, shaft 91 being mechanically coupled to carriage 97 for vertical movement into and out of vessel 23 but being free to move rotationally relative to carriage 97. Rotation of shaft 91 is provided by a motor 99 controlled by computer 29. Carriage 97 is slidably mounted on a pair of posts 101-1 and 101-2. Vertical movement of carriage 97 along posts 101-1 and 101-2 is achieved by means of a threaded drive shaft 103 mechanically coupled to a motor 105 controlled by computer 29.

Figure 15:
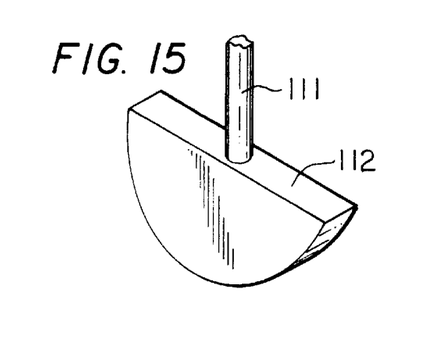
FIG. 15 is a fragmentary perspective view of a paddle shaft which may be used instead of the basket shaft in the apparatus of FIG. 1.

As discussed elsewhere in the present specification, apparatus 11 can be used either for basket-type or paddle-type dissolution of tablets. When apparatus 11 is intended for basket-type dissolution, tablet-containing baskets 45 are loaded into carousel 39 and basket shaft 91 is attached to carriage 97. When apparatus 11 is intended for paddle-type dissolution, tablets are placed directly into compartments 43 and basket shaft 91 is replaced with a paddle shaft 111 having a paddle 112 at the bottom end thereof (see FIG. 15).

An opening 113 is provided in platform 21, opening 113 being aligned with basket shaft 91 (or paddle shaft 111) and having a shape appropriate for insertion of basket shaft 91 (or paddle shaft 111) therethrough.

Figure 1:
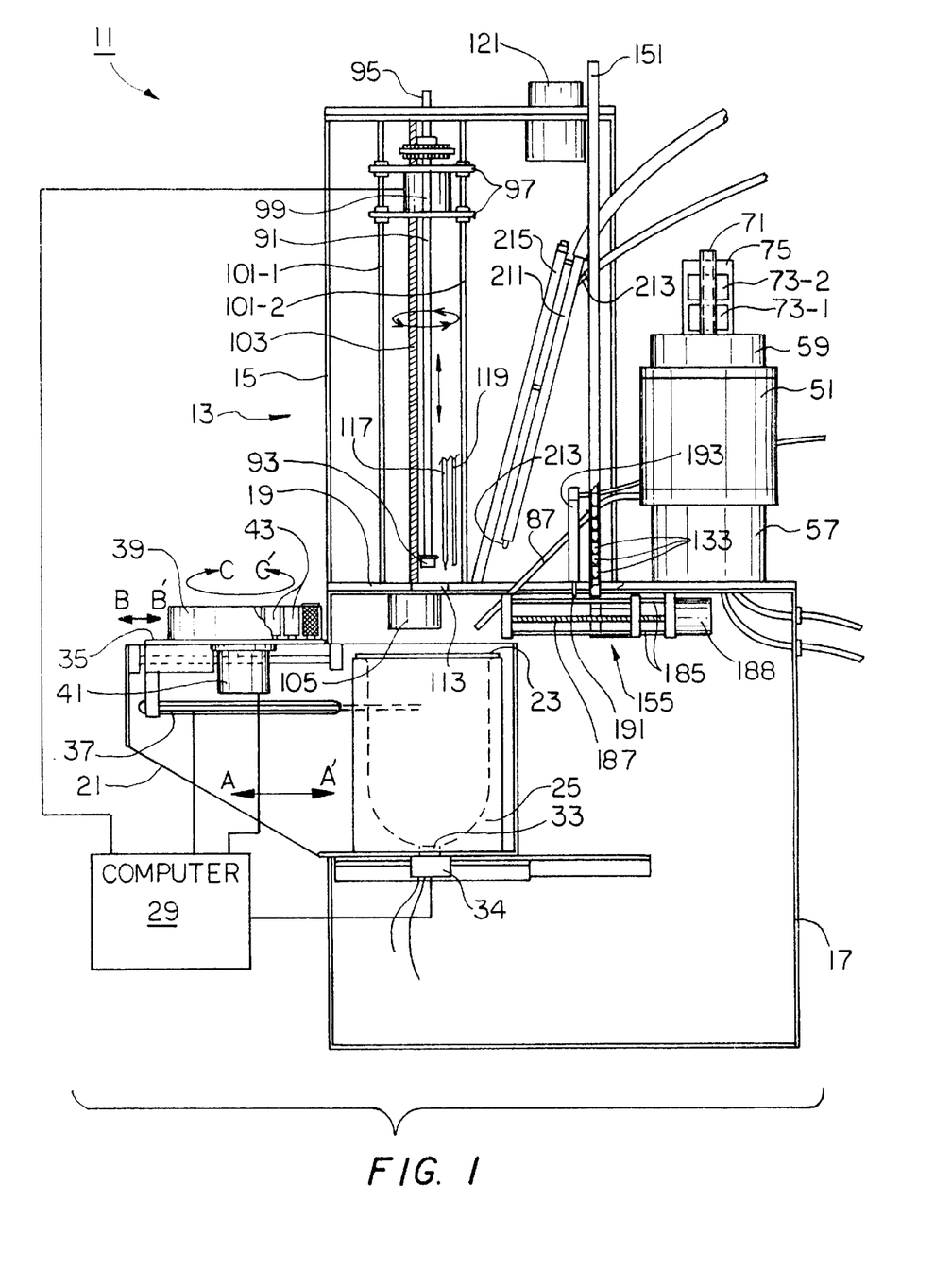
FIG. 1 is a simplified, partly schematic, side elevation view, broken away in part, of one embodiment of an automated tablet dissolution apparatus constructed according to the teachings of the present invention, certain aspects of the automated tablet dissolution apparatus not being shown to improve clarity.
Figure 2:
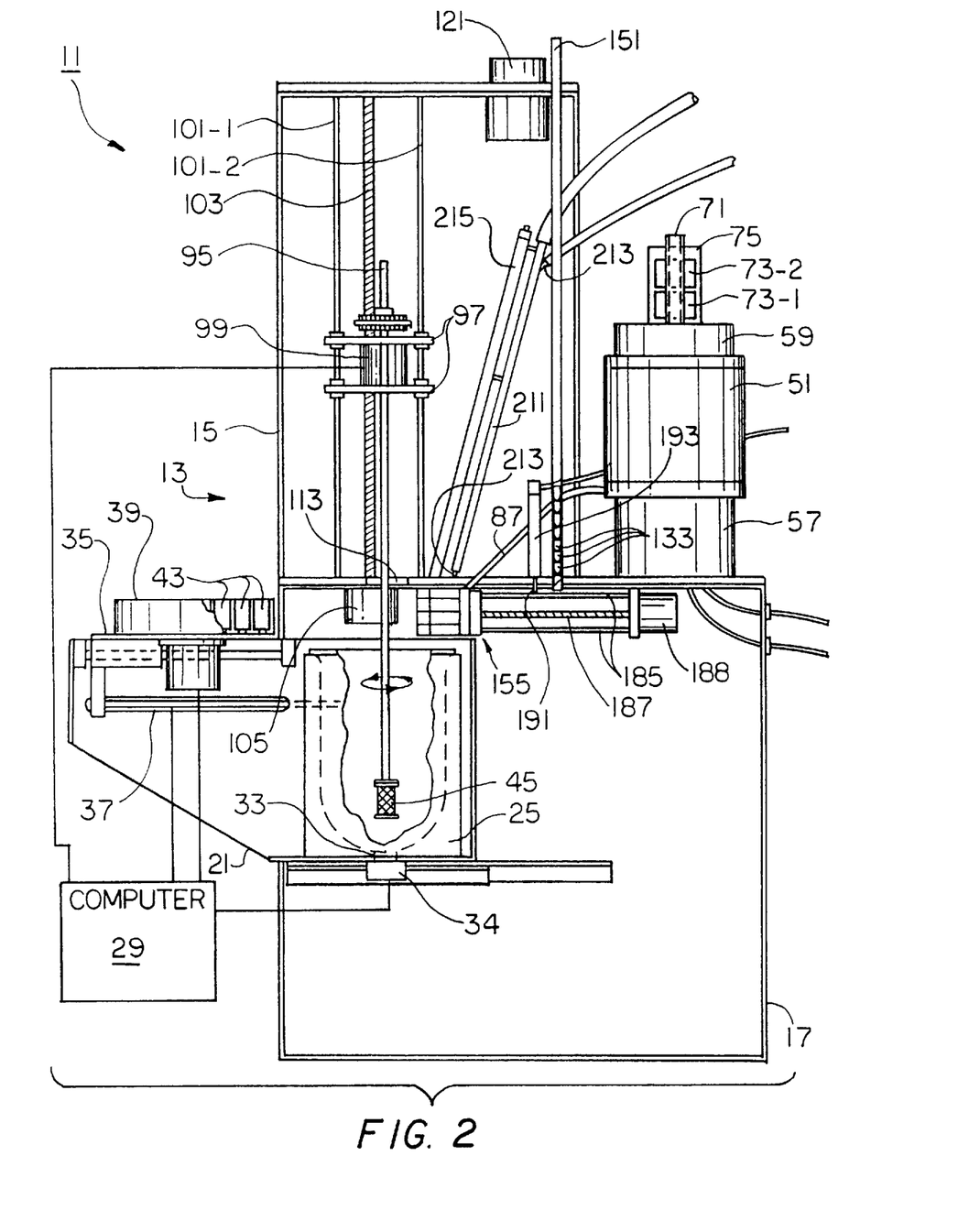
FIG. 2 is a simplified, partly schematic, side elevation view, broken away in part, of the automated tablet dissolution apparatus of FIG. 1, depicting the automated tablet dissolution apparatus during the tablet dissolution stage of its operation, certain aspects of the automated tablet dissolution apparatus not being shown to improve clarity.
Figure 3:
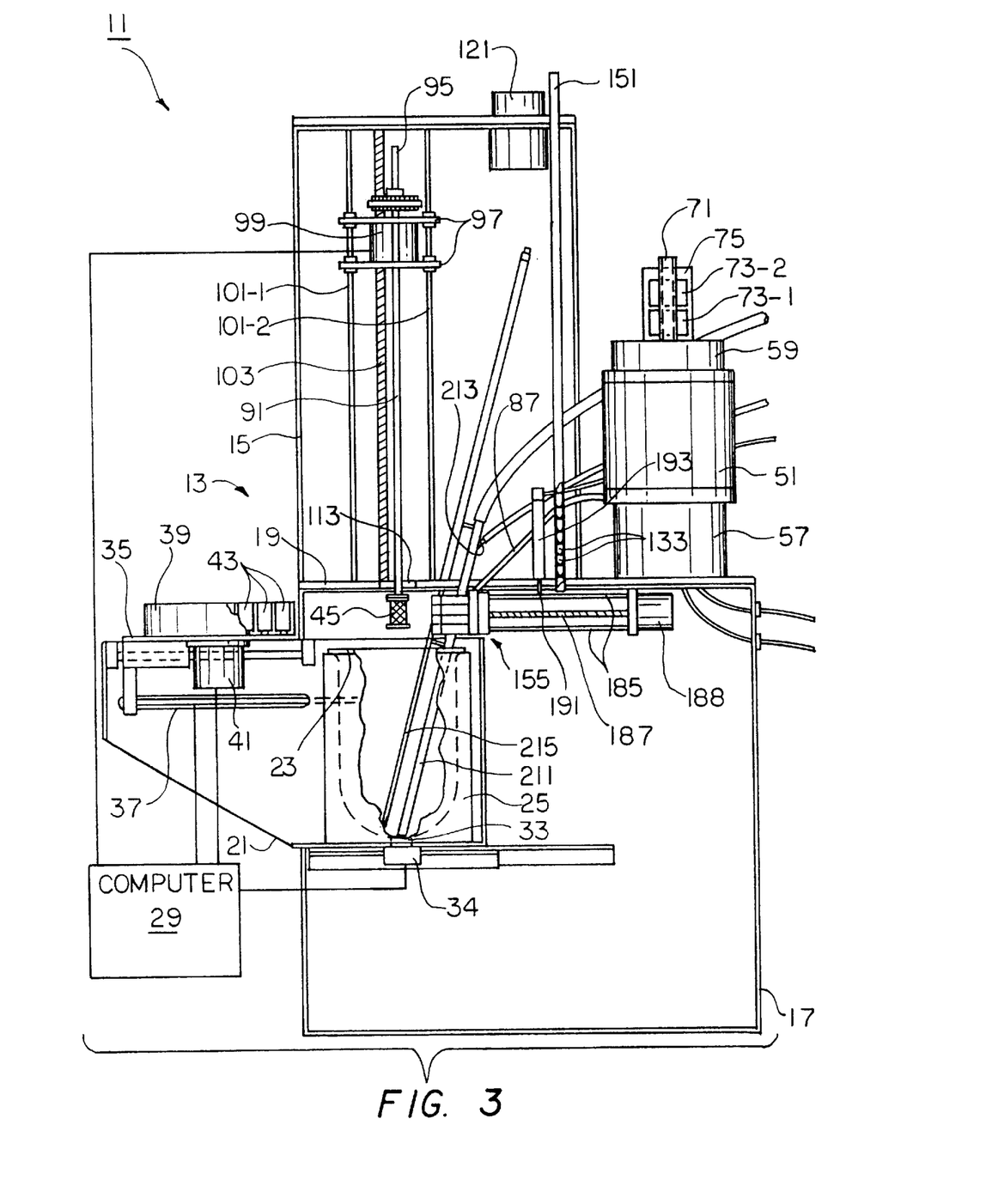
FIG. 3 is a simplified, partly schematic, side elevation view, broken away in part, of the automated tablet dissolution apparatus of FIG. 1, depicting the automated tablet dissolution apparatus during the media removal stage of its operation, certain aspects of the automated tablet dissolution apparatus not being shown to improve clarity.
Figure 4:
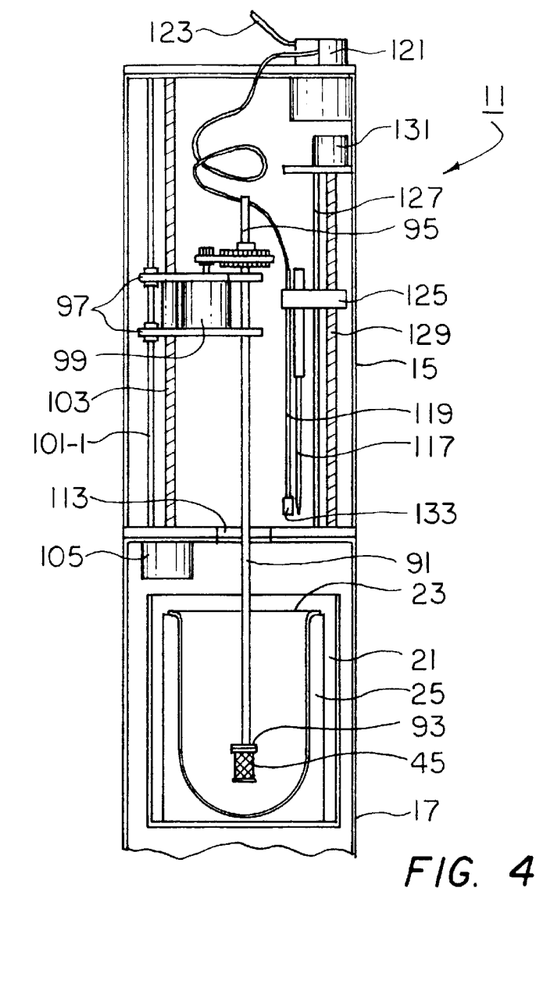
FIG. 4 is a simplified schematic front view of the automated tablet dissolution apparatus of FIG. 1, depicting the automated tablet dissolution apparatus during the tablet dissolution stage of its operation, certain aspects of the automated tablet dissolution apparatus not being shown to improve clarity.
Figure 5:
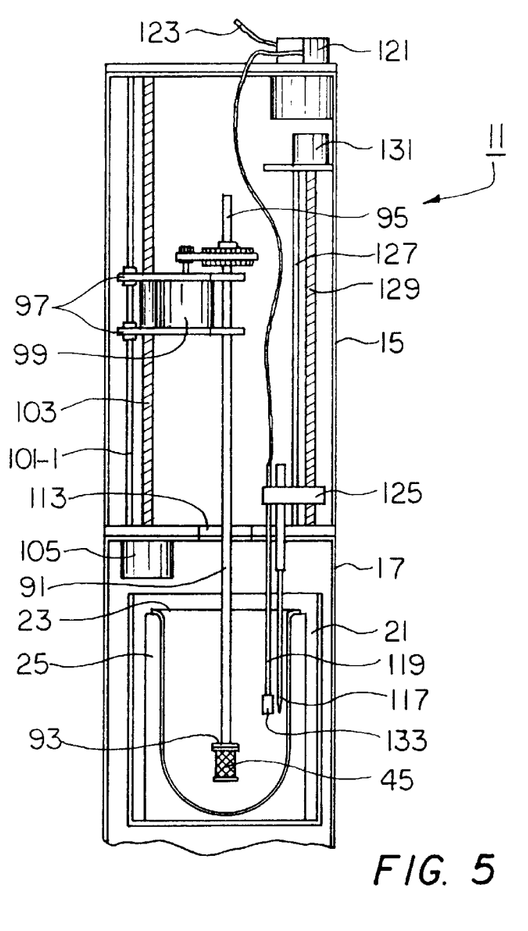
FIG. 5 is a simplified schematic front view of the automated tablet dissolution apparatus of FIG. 1, depicting the automated tablet dissolution apparatus during the media sampling stage of its operation, certain aspects of the automated tablet dissolution apparatus not being shown to improve clarity.

Referring now to FIGS. 4 and 5, apparatus 11 further comprises a temperature sensor 117 and a media sampling cannula 119. Sensor 117 is connected to computer 29 so as to provide computer 29 with temperature readings of the dissolution media within vessel 23. Cannula 119 is used to withdraw samples of the media within vessel 23 for external analysis (e.g., chromatography, spectroscopy, etc.) and is connected to a peristaltic pump 121 through a length of flexible tubing 123. Pump 121 is controlled by computer 29. Sensor 117 and cannula 119, both of which are vertically aligned with vessel 23, are fixedly attached near their respective top ends to a carriage 125. Carriage 125, in turn, is slidably mounted on a pair of posts 127. Vertical movement of carriage 125 along posts 127 to permit sensor 117 and cannula 119 to be moved into and out of vessel 23 is achieved by means of a threaded drive shaft 129 mechanically coupled to a motor 131 controlled by computer 29.

As seen in FIGS. 4 and 5, a disposable depth filter 133 is mounted on the bottom end of cannula 119. Filter 133, which may be a conventional depth filter of the type used in tablet dissolution, is used to remove pharmacologically-inactive excipients from the sample collected for analysis using cannula 119. Filter 133 preferably has a pore size of approximately 2 microns.

Referring now to FIGS. 1 through 3 and 16(a) through 16(e), apparatus 11 can be seen to further include means for feeding a filter 133 onto the bottom of cannula 119 and for ejecting from cannula 119 a filter 133 that has been loaded thereonto and no longer needed. In the present embodiment, said feeding and ejecting means comprises a tube 151 into which a plurality of filters 133 have previously been stacked, either manually or otherwise. As seen best in FIGS. 16(a) through 16(e), filters 133 are held in place by an air cylinder 153 (controlled by computer 29) which releasably engages the bottom filter 133 of the stack within tube 151. Said feeding and ejecting means also comprises a carriage assembly 155. Carriage assembly 155 includes a filter receiving member 157. Member 157 is provided with a transverse bore 159 alignable with tube 151 and appropriately dimensioned to receive a filter 133. Member 157 is also provided with a longitudinal slot 161 (see FIG. 19) which extends rearwardly from the front of member 157 into bore 159 and which is appropriately dimensioned, for reasons to become apparent below, to accommodate cannula 119 extending transversely therethrough.

Carriage assembly 155 also includes a base 167, member 157 being mounted on base 167. Base 167 is provided with a transverse bore 168 aligned with bore 159 of member 157 and similarly dimensioned to receive filter 133. As seen best in FIGS. 17(a) and 19, base 167 is also provided with a longitudinal slot 169, which extends rearwardly from the front of base 167 into bore 168 and which is also appropriately dimensioned to accommodate cannula 119 extending transversely therethrough. Carriage assembly 155 also includes a filter stop 171 (shown in isolation in FIGS. 18(a) and 18(b)), which is slidably mounted within longitudinal slot 169 of base 167. Movement of stop 171 within slot 169 is achieved by means of an air cylinder 173, one end of which is inserted into an opening 175 formed in stop 171. Stop 171 is shaped to include a platform 181 which, when positioned between bore 159 of member 157 and bore 168 of base 167, prevents a filter 133 from passing therebetween.

As seen best in FIGS. 1 through 3, 17(a), 17(b) and 19, carriage assembly 155 further includes a block 183 to which base 167 and member 157 are fixedly attached. Block 183, in turn, is slidably mounted on a pair of posts 185. Movement of block 183 along posts 185 is achieved by means a threaded drive shaft 187 mechanically coupled to a motor 188 controlled by computer 29.

Figure 16A:
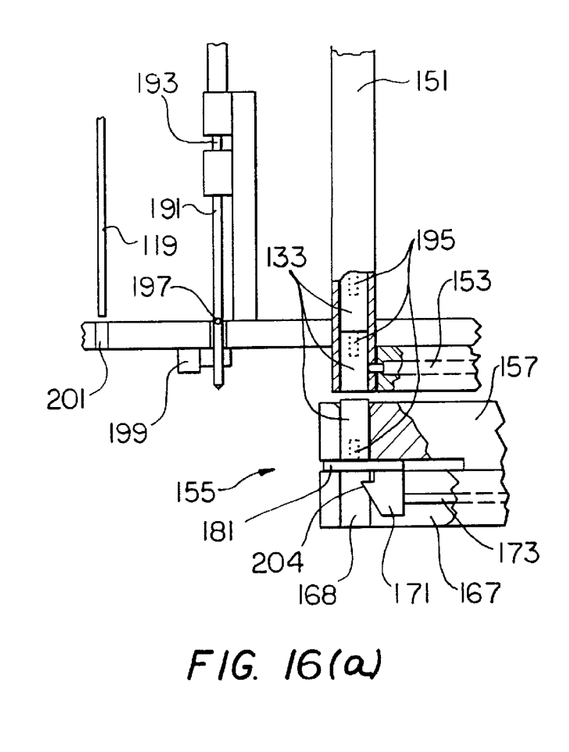
FIGS. 16(a) through 16(e) are fragmentary side elevation views, partly in section and broken away in part, illustrating the operation of the depth filter feeding and ejecting mechanism of the apparatus of FIG. 1.
Figure 16B:
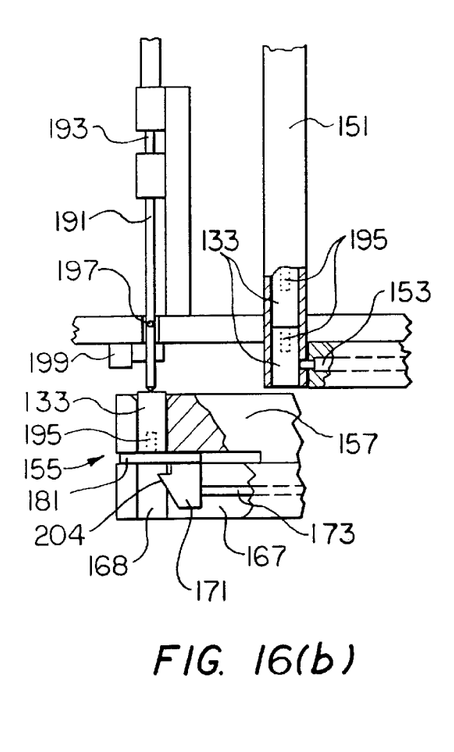
Figure 16C:
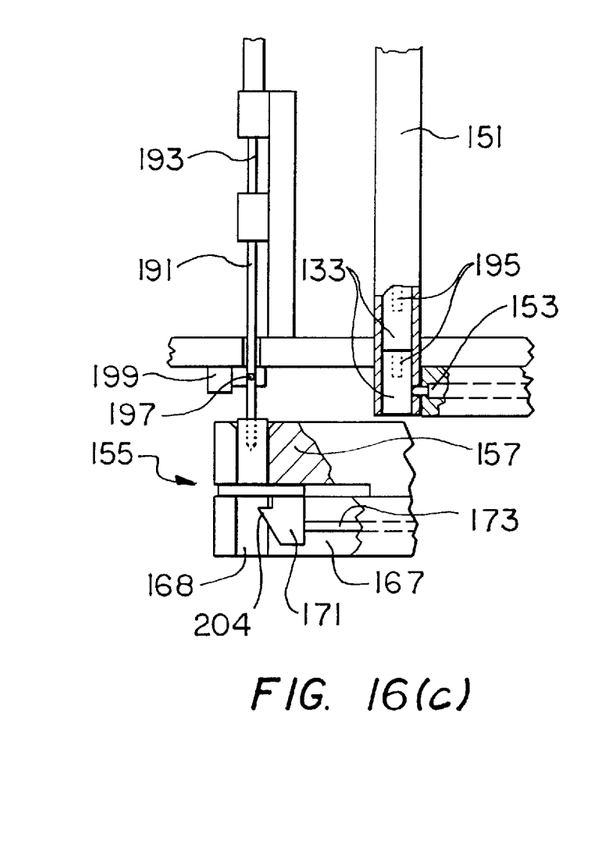
Figure 16D:
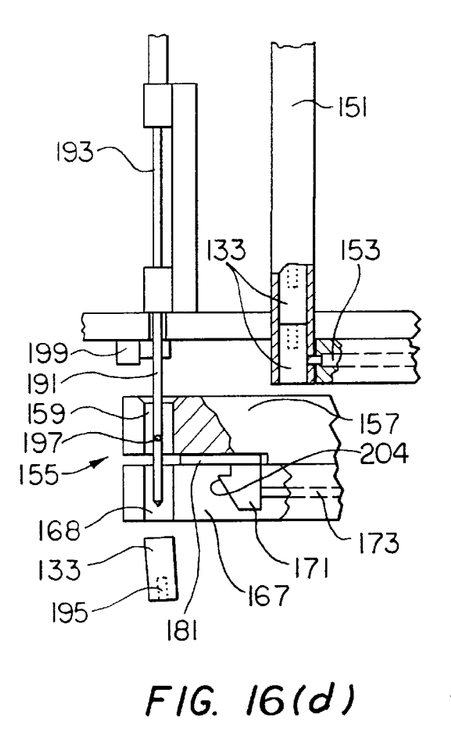
Figure 16E:
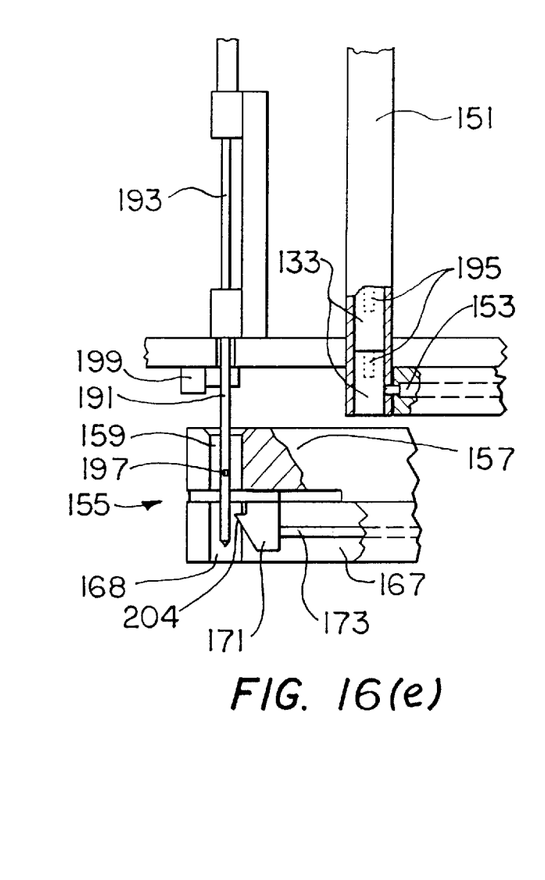

Referring back now to FIGS. 16(a) through 16(e), there is illustrated the manner in which the filter feeding and ejecting means ensures that a filter 133 is properly positioned for feeding onto the end of cannula 119. As seen in FIG. 16(a), the temporary retraction of air cylinder 153 allows the bottom filter 133 in tube 151 to drop into bore 159 of member 157. Because stop 171 is positioned so that platform 181 is located between bores 159 and 168, filter 133 is retained within bore 159. In FIG. 16(b), carriage assembly 155 moves laterally in the direction of cannula 119 until bores 159 and 168 are in alignment with a probe 191. Probe 191, which is used to determine whether filter 133 has been loaded into bore 159 correctly (i.e., with its cannula opening 195 facing upwardly) or incorrectly (i.e., with its cannula opening 195 facing downwardly or not loaded at all), is vertically movable by means of an air cylinder 193 controlled by computer 29. Probe 191 is provided with an opening 197, which is detected by an optic sensor 199 if probe 191 extends downwardly to an appropriate depth (see FIG. 16(c)). If, however, as is the case shown in FIG. 16(b), filter 133 is positioned upside down in bore 159, probe 191 will not be able to extend down far enough for sensor 199 to detect hole 197. In such a case, as seen in FIG. 16(d), filter stop 171 will then be retracted and filter 133 will be ejected through bores 159 and 168 into a filter refuse receptacle (not shown). As seen in FIG. 16(e), if no filter has been loaded into bore 159, probe 191 will pass through an opening 200 (see FIG. 18(a)) in filter stop 171 and will move downwardly too far for hole 197 to be detected by sensor 199.

Assuming that filter 133 is properly positioned within bore 159, filter 133 is fed onto cannula 119 as follows: Carriage assembly 155 moves laterally from the aforementioned testing area to a point where cannula hole 195 of filter 133 is aligned with cannula 119. Cannula 119 moves downwardly through an opening 201 in platform 21 into cannula hole 195 until it frictionally engages filter 133 and then moves upwardly a sufficient distance to remove filter 133 from member 157. Carriage assembly 155 then retracts, leaving filter 133 on the bottom end of cannula 119.

Filter 133 is removed from cannula 119 (e.g., after the media has been sampled) as follows: With cannula 119 and filter 133 remaining lowered beyond the height of carriage assembly 155, carriage assembly 155 is moved back to the aforementioned filter loading position, thereby causing cannula 119 to pass through slots 161 and 169 of member 157 and base 167, respectively, until it extends through bores 159 and 168. Cannula 119 is then raised, causing filter 133 to be drawn upwardly through bore 168. As filter 133 moves upwardly through bore 168, however, it becomes wedged in bore 168 against a flange 204 of filter stop 171 and cannot continue upwardly any further. Upward movement of cannula 119, however, is unimpeded; consequently, cannula 119 slips out of filter 133 and is retracted to its initial position. Carriage assembly 155 then moves back over to the filter testing area. Probe 191 then moves downwardly, pushing filter 133 down through bore 168 where it is discarded into the filter refuse receptacle (not shown).

Figure 17A:
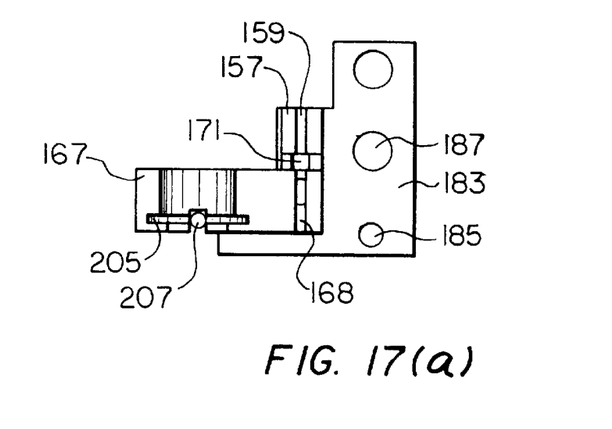
FIGS. 17(a) and 17(b) are front and top views, respectively, of the carriage assembly of the depth filter feeding and ejecting mechanism of FIGS. 16(a) through 16(e)
Figure 17B:
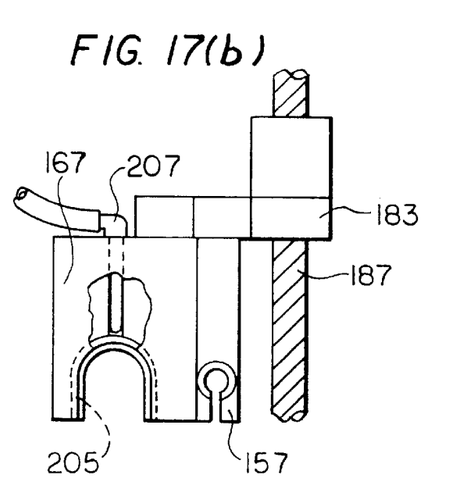
Figures 18A, 18B:
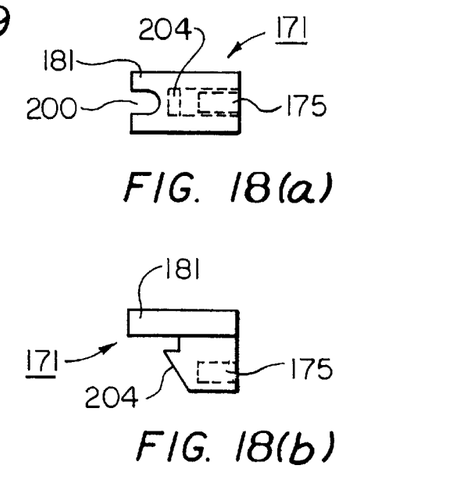
FIGS. 18(a) and 18(b) are top and side elevation views, respectively, of the plunger shown in FIGS. 16(a) through 16(e)
Figure 19:
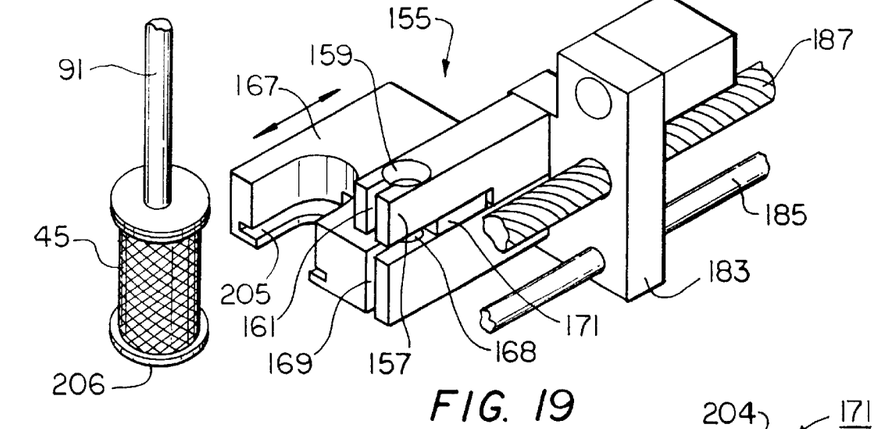
FIG. 19 is a perspective view illustrating how the carriage assembly of the depth filter feeding and ejecting mechanism can also be used to detach a basket from the basket shaft.

Referring now to FIGS. 17(a), 17(b) and 19, base member 167 can also be seen to be shaped to include an arcuate groove 205 adapted to receive a bottom lip 206 of basket 45. Consequently, basket 45 can be detached from shaft 91 by moving base member 167 relative to basket 45 until lip 206 is inserted into groove 205 and then pulling shaft 91 upwardly until lid 93 disengages from basket 45. Carriage assembly 155, with basket 45 in tow, is then moved laterally to the filter testing position, where an ejector rod 207 pushes basket 45 out of groove 205 into a basket receptacle (not shown).

Referring back now to FIGS. 1 through 3, apparatus 11 further comprises means for emptying media from vessel 23. In the present embodiment, said vessel emptying means comprises a relatively large diameter tube 211 and a relatively small diameter tube 213, tube 213 being fixedly mounted within tube 211 and extending a short distance out from the bottom of tube 211. The top ends of tubes 211 and 213 are connected to a pump motor (not shown) through a pair of pump heads (not shown). Tube 211 is mechanically coupled to an air cylinder 215, which is controlled by computer 29. Air cylinder 215 serves to move tube 211 into and out of vessel 23. Tube 211 is capable of quickly removing large quantities of media from vessel 23 whereas tube 213 is capable of removing small quantities of media from vessel 23 that tube 211 may leave behind.

Although not shown, apparatus 11 also comprises means, controlled by computer 29, for dispensing a washing solution into vessel 23. Washing solution may also be emptied from vessel 23 using the aforementioned vessel emptying means.

To use apparatus 11 for basket-type dissolution, a user places one or more baskets 45 into compartments 43 of carousel 39 and places a tablet inside each basket 45. The user also mounts basket shaft 91 on carriage 97. In addition, the user inputs information into computer 29 regarding several dissolution testing parameters, such as the number of tablets to be tested, whether the dissolution is a basket-type dissolution or a paddle-type dissolution, the time duration of each dissolution, the number of samples to be drawn from each dissolution, the times at which said samples are to be taken, the temperature at which dissolution is to be performed, etc. The dissolution testing parameters may be either the same or different for multiple tablets tested sequentially.

From this point onward, no more human intervention is necessary as apparatus 11 automatically performs the following steps, among others: The media dispensing means volumetrically measures the desired quantity of media, pre-heats and sparges said quantity of media and then dispenses the pre-heated and sparged quantity of media into vessel 23. The media within vessel 23 is then maintained at the appropriate dissolution temperature by platen 25. Carousel 39 is positioned so that a compartment 43 holding a tablet-containing basket 45 is situated directly under shaft 91. Shaft 91 is then lowered until lid 93 engages basket 45. Shaft 91 is then raised, thereby removing basket 45 from carousel 39. Carousel 39 is then moved to its forwardmost position, and shaft 91 is lowered until basket 45 is positioned approximately 1 inch from the bottom of vessel 23. Basket 45 is then rotated at approximately 50–150 rpm for the dissolution period specified (see FIG. 2). A filter 133 is fitted onto cannula 119 and, at the time specified, a sample is withdrawn from vessel 23. Where multiple samples are taken during the dissolution period, either the same filter 133 or different filters 133 may be used. After use, the filter 133 is removed from cannula 119 and discarded. At the conclusion of the dissolution period, rotation of basket 45 is halted and shaft 91 is raised until lip 206 of basket 45 is vertically aligned with groove 205 of base member 167. Base member 167 is then moved laterally towards basket 45 until lip 206 is inserted into groove 205. Shaft 91 is then raised, thereby detaching shaft 91 from basket 45. Base member 167 then moves back laterally, causing ejector rod 207 to eject basket 45 from base member 167 into a used basket receptacle. At the same time that basket 45 is being detached from shaft 91, tubes 211 and 213 are lowered into vessel 23 and are used to remove the media from vessel 23 (see FIG. 3). While this is being done, a washing solution is dispensed into vessel 23, tubes 211 and 213 similarly being used to remove the washing solution from vessel 23. Lid 93 of shaft 91 may be lowered into vessel 23 to also be washed by the washing solution. At the conclusion of the above-described procedure, shaft 91 and carriage assembly 155 are returned to their initial positions. Where a second dissolution is to be performed, carousel 39 is then positioned so that a second basket 45 is aligned with shaft 91 and the foregoing procedure is repeated.

To use apparatus 11 for paddle-type dissolution, the above-described procedure is performed with the following exceptions: Instead of attaching shaft 91 to carriage 97, the user attaches paddle shaft 111 to carriage 97. Moreover, instead of placing tablets inside baskets 45 that are, in turn, inserted into carousel 39, the user places the tablets directly into compartments 43 of carousel 39. The tablets are then dispensed from carousel 39 into vessel 29 in the manner shown in FIG. 12. Because the same paddle 112 and paddle shaft 111 are used for each dissolution, the basket-basket shaft detachment procedure described above is not applicable.

As can readily be appreciated, two or more independently operable apparatuses 11 can be hooked up to same computer 29.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A tablet dissolution apparatus comprising:
   (a) a dissolution vessel;
   (b) a kit of mechanically-rotatable means alternately positionable in said dissolution vessel for agitating the contents of said dissolution vessel, said kit comprising
      (i) a first mechanically-rotatable means, said first mechanically-rotatable means comprising a paddle and
      (ii) a second mechanically-rotatable means, said second mechanically-rotatable means comprising a cage-type basket;
   (c) means for rotating one of said first and said second mechanically-rotatable means in said dissolution vessel; and
   (d) automated means for sampling the contents of said dissolution vessel.

2. The tablet dissolution apparatus as claimed in claim 1 further comprising automated means for volumetrically-obtaining, heating and sparging a quantity of media and for dispensing said quantity of media into said dissolution vessel.

3. The tablet dissolution apparatus as claimed in claim 1 wherein said automated sampling means comprises a cannula having a sampling end insertable into the dissolution vessel and wherein said tablet dissolution apparatus further comprises automated means for loading and ejecting a depth filter onto and off of the sampling end of said cannula.

4. The tablet dissolution apparatus as claimed in claim 3 wherein said automated loading and ejecting means comprises automated means for testing the orientation of a depth filter relative to said cannula prior to attempting to attach the depth filter to said cannula.

5. The tablet dissolution apparatus as claimed in claim 1 further comprising automated means for dispensing a tablet into said dissolution vessel.

6. The tablet dissolution apparatus as claimed in claim 1 further comprising automated means for heating said dissolution vessel, said automated heating means comprising a platen appropriately dimensioned to removably receive said dissolution vessel.

7. The tablet dissolution apparatus as claimed in claim 1 further comprising automated means for emptying the contents of said dissolution vessel, said automated means comprising a comparatively large diameter tube and a comparatively small diameter tube, said comparatively small diameter tube being positioned inside of and extending a short distance out of the bottom of the comparatively large diameter tube.

8. The tablet dissolution apparatus as claimed in claim 1 further comprising means for imaging the contents of the dissolution vessel.

9. A tablet dissolution apparatus comprising:
   (a) a dissolution vessel;
   (b) mechanically-rotating means positionable in said dissolution vessel for agitating the contents of said dissolution vessel;
   (c) a cannula, said cannula having a sampling end insertable into said dissolution vessel for use in withdrawing a sample from the dissolution vessel;
   (d) automated means for mounting a depth filter on the sampling end of said cannula; and
   (e) automated means for volumetrically-obtaining heating and sparging a quantity of media and for dispensing said quantity of media into said dissolution vessel.

10. The tablet dissolution apparatus as claimed in claim 9 further comprising automated means for inserting the sampling end of said cannula into the dissolution vessel and for withdrawing a sample therethrough.

11. The tablet dissolution apparatus as claimed in claim 9 further comprising automated means for removing a depth filter mounted on the sampling end of said cannula.

12. The tablet dissolution apparatus as claimed in claim 9 further comprising platen means, dimensioned to removably receive said dissolution vessel, for heating said dissolution vessel.

13. The tablet dissolution apparatus as claimed in claim 12 wherein said platen means comprises a metallic platen.

14. A tablet dissolution apparatus comprising:
   (a) a dissolution vessel;
   (b) a cage-type basket adapted to hold a tablet;
   (c) a rotatable shaft aligned with said dissolution vessel and vertically movable between a first vertical position above said dissolution vessel and a second vertical position within said dissolution vessel, said rotatable shaft having a bottom end adapted to removably engage said cage-type basket;
   (d) a stage, said cage-type basket being disposed on said stage, said stage being movable between a first translational position wherein said cage-type basket is translationally aligned with said dissolution vessel and the bottom end of said rotatable shaft and is vertically disposed between said dissolution vessel and said rotatable shaft in said first vertical position and a second translational position wherein said stage is not translationally aligned with said rotatable shaft;
   (e) automated means for moving said stage between said first translational position and said second translational position;
   (f) automated means for vertically moving said rotatable shaft between said first vertical position and an intermediate vertical position wherein the bottom end of said rotatable shaft is positioned to engage said cage-type basket when said stage is disposed in said first translational position and for vertically moving said rotatable shaft between said intermediate vertical position and said second vertical position when said stage is disposed in said second translational position: and (g) automated means for rotating said rotatable shaft.

15. The tablet dissolution apparatus as claimed in claim 14 further comprising automated means for disengaging said cage-type basket from the bottom end of said rotatable shaft.

16. A tablet dissolution apparatus comprising:

(a) a dissolution vessel;

(b) a rotatable shaft aligned with said dissolution vessel and vertically movable between a first vertical position above said dissolution vessel and a second vertical position within said dissolution vessel, said rotatable shaft having a bottom end adapted to removably engage a cage-type basket;

(c) a rotatable carousel, said rotatable carousel having a plurality of compartments, each of said compartments adapted to hold a cage-type basket;

(d) a plurality of cage-type baskets, each of said cage-type baskets being disposed in a compartment of said rotatable carousel, each of said cage-type baskets being adapted to hold a tablet;

(e) a stage, said rotatable carousel being disposed on said stage, said stage being movable between a first translational position wherein a compartment of said rotatable carousel is translationally aligned with said dissolution vessel and the bottom end of said rotatable shaft and is vertically disposed between said dissolution vessel and said rotatable shaft in said first vertical position and a second translational position wherein said stage is not translationally aligned with said rotatable shaft;

(f) automated means for moving said stage between said first translational position and said second translational position;

(g) automated means for vertically moving said rotatable shaft between said first vertical position and an intermediate vertical position wherein the bottom end of said rotatable shaft is positioned to engage a cage-type basket disposed in a compartment of said rotatable carousel when said stare is disposed in said first translational position and for vertically moving said rotatable shaft between said intermediate vertical position and said second vertical position when said stage is disposed in said second translational position;

(h) automated means for rotating said rotatable carousel when said stage is in said first translational position to align a compartment of said rotatable carousel with the bottom end of said rotatable shaft;

(i) automated means for disengaging a used cage-type basket from the bottom end of said rotatable shaft; and (j) automated means for rotating said rotatable shaft.

17. The tablet dissolution apparatus as claimed in claim 16 further comprising means for dispensing a quantity of media into said dissolution vessel.

18. The tablet dissolution apparatus as claimed in claim 16 further comprising means for sampling the contents of the dissolution vessel.

19. The tablet dissolution apparatus as claimed in claim 18 wherein said sampling means comprises a cannula having a sampling end insertable into the dissolution vessel and wherein said tablet dissolution apparatus further comprises means for loading and ejecting a depth filter onto and off of the sampling end of said cannula.

20. The tablet dissolution apparatus as claimed in claim 19 further comprising means for emptying the contents of said dissolution vessel.

21. The tablet dissolution apparatus as claimed in claim 20 further comprising means for heating the dissolution vessel.

22. The tablet dissolution apparatus as claimed in claim 21 wherein said media dispensing means, said sampling means, said loading and ejecting means, said emptying means and said heating means are all fully automated.

23. A tablet dissolution apparatus comprising:

(a) a dissolution vessel, said dissolution vessel defining a space in which a quantity of media and a tablet may be placed;

(b) media preheating and dispensing means for preheating a quantity of media to a temperature approximating that desired for dissolution and for dispensing said quantity of preheated media at a desired dissolution temperature into said dissolution vessel;

(c) means for heating the contents of said dissolution vessel so as to keep the contents of said dissolution vessel at said desired dissolution temperature; and (d) means for agitating the contents of said dissolution vessel.

24. The tablet dissolution apparatus as claimed in claim 23 further comprising means for volumetrically determining the quantity of media to be preheated and dispensed by said media preheating and dispensing means.

25. A tablet dissolution apparatus comprising:

(a) a dissolution vessel;

(b) mechanically-rotating means positionable in said dissolution vessel for agitating the contents of said dissolution vessel;

(c) a cannula having a sampling end insertable into said dissolution vessel for use in withdrawing a sample from the dissolution vessel;

(d) automated means for loading and ejecting a depth filter onto and off of the sampling end of said cannula; and (e) automated means for testing the orientation of a depth filter relative to said cannula prior to attempting to attach the depth filter to said cannula.

* * * * *